United States Patent
Yoon et al.

(10) Patent No.: US 10,221,227 B2
(45) Date of Patent: Mar. 5, 2019

(54) PEPTIDE FOR PROMOTING OSTEOGENIC DIFFERENTIATION OR VASCULARIZATION AND USE THEREOF

(71) Applicants: INDUSTRY FOUNDATION OF CHONNAM NATIONAL UNIVERSITY, Gwangju (KR); CHONNAM NATIONAL UNIVERSITY HOSPITAL, Gwangju (KR)

(72) Inventors: Taek Rim Yoon, Gwangju (KR); Hyung Keun Kim, Gwangju (KR); Jong Keun Seon, Gwangju (KR); Ji Hyun Kim, Gwangju (KR); Ju Yeon Kang, Gwangju (KR)

(73) Assignees: INDUSTRY FOUNDATION OF CHONNAM NATIONAL UNIVERSITY, Gwangju (KR); CHONNAM NATIONAL UNIVERSITY HOSPITAL, Gwangju (KR)

(*) Notice: Subject to any disclaimer, the term of this patent is extended or adjusted under 35 U.S.C. 154(b) by 0 days.

(21) Appl. No.: 15/137,112

(22) Filed: Apr. 25, 2016

(65) Prior Publication Data
US 2016/0318984 A1  Nov. 3, 2016

(30) Foreign Application Priority Data
Apr. 28, 2015 (KR) .................. 10-2015-0059575

(51) Int. Cl.
*A61K 38/03* (2006.01)
*C07K 14/52* (2006.01)
*C12N 5/077* (2010.01)
*A61K 38/00* (2006.01)

(52) U.S. Cl.
CPC .......... *C07K 14/521* (2013.01); *C07K 14/522* (2013.01); *C12N 5/0654* (2013.01); *A61K 38/00* (2013.01); *C12N 2501/998* (2013.01)

(58) Field of Classification Search
CPC ............................. A61K 2300/00; A61K 38/10
See application file for complete search history.

(56) References Cited

U.S. PATENT DOCUMENTS

| 2011/0020375 A1 | 1/2011 | Chu et al. |
| 2011/0207166 A1 | 8/2011 | Vaiselbuh |
| 2014/0288010 A1* | 9/2014 | Hill ...................... A61K 38/195 514/21.3 |

FOREIGN PATENT DOCUMENTS

| WO | 2006124013 A2 | 11/2006 |
| WO | WO 2006124013 A2 * | 11/2006 ........... C07K 14/522 |

OTHER PUBLICATIONS

NCBI, NCBI Reference Sequence, accessed on Apr. 28, 2017. available online at: https://www.ncbi.nlm.nih.gov/protein/296011023?report=genbank&log$=protalign&blast_rank=1&RID=G6TCN1M8015.*
Office action dated Nov. 10, 2016 from Korean Intellectual Property Office in a counterpart Korean Patent Application No. 10-2015-0059575.
International Search Report for PCT/KR2016/004346 dated Aug. 2, 2016.
Gina Lisignoli et al., "CXCL12 (SDF-1) and CXCL13 (BCA-1) Chemokines Significantly Induce Proliferation and Collagen Type I Expression in Osteoblasts From Osteoarthritis Patients", Journal of Cellular Physiology vol. 206, pp. 78-85, 2006.
Seiji Mishima et al., "Effective ex vivo expansion of hematopoietic stem cells using osteoblast-differentiated mesenchymal stem cells is CXCL12 dependent", European Journal of Haematology, vol. 84, pp. 538-546, 2010.
European Search Report for EP16786718.3 from European patent office in a counterpart European patent application dated Aug. 16, 2018.
Gronthos et al: "The role of the chemokine CXCL 12 in osteoclastogenesis", Trends in Endocrinology and Metabolism, Elsevier Science Publishing, New York, NY, US, vol. 18, No. 3, pp. 108-113, 2007.
Yu X et al: "Stromal Cell-Derived Factor-1 (SDF-1) Recruits Osteoclast Precursors by Inducing Chemotaxis, Matrix Metalloproteinase-9 (MMP-9) Activity, and Collagen Transmigration", Journal of Bone and Mineral Research, Blackwell Science, Inc, US, vol. 18, No. 8, 2003.

* cited by examiner

*Primary Examiner* — Rachael E Bredefeld
*Assistant Examiner* — Kaipeen E Yang
(74) *Attorney, Agent, or Firm* — The PL Law Group, PLLC (57) ABSTRACT

A peptide has the amino acid sequence of SEQ ID NO: 1. The peptide exhibits the activity of a differentiation factor by promoting differentiation by acting on osteoblasts or vascular endothelial cells. Additionally, the peptide can be used for ameliorating or treating the diseases or conditions of effectiveness of osteogenic differentiation factor or bone morphogenetic factor or vascularization factor.

6 Claims, 4 Drawing Sheets

Specification includes a Sequence Listing.

FIG. 1

Pro-Pro-Arg-Ala-Cys-Pro-Thr-Ala-Arg-Ala-Leu-Cys-Glu-Ile-Arg
(P-P-R-A-C-P-T-A-R-A-L-C-E-I-R)

(SEQ ID NO: 1)

```
                         SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: BFP 5 derived from stromal cell-derived factor
      1

<400> SEQUENCE: 1

Pro Pro Arg Ala Cys Pro Thr Ala Arg Ala Leu Cys Glu Ile Arg
1               5                   10                  15
```

PEPTIDE FOR PROMOTING OSTEOGENIC DIFFERENTIATION OR VASCULARIZATION AND USE THEREOF

CROSS-REFERENCE TO RELATED APPLICATION

The present application claims priority to Korean Patent Application No. 10-2015-0059575, filed on Apr. 28, 2015, the disclosure of which is incorporated herein by reference in its entirety.

BACKGROUND

1. Technical Field

The present invention relates to a protein effective in promoting osteogenic differentiation and vascularization, and more specifically, to a peptide exhibiting the activities of promoting osteogenic differentiation or vascularization, and a use thereof.

2. Background Art

Bone decrease is greatly influenced by the change in bone mass. The major factors that affect the change in bone mass include genetic factors, nutrients intake, hormonal change, exercise, and difference in lifestyle, etc. Recently, aging, lack of exercise, low-calcium diet, menopause, ovariectomy, etc., have been known to cause the decrease in bone mass and thereby induce osteoporosis.

Osteoporosis is a disease in which the bones become very weak along with the progress of the symptoms that calcareous deposit in bone tissue decreases, bone density becomes low and medullary cavity becomes wide, thereby easily causing the occurrence of bone-related diseases such as bone fracture even with a slight shock.

Although there is an individual difference, the bone resorption level is lower in black people than in white people and thus black people have higher bone mass. Generally, bone mass reaches the highest level at age between 14 and 18 and decreases about 1% per year at old ages. In particular, bone decrease continuously occurs in women since age 30 and at menopause bone decrease proceeds rapidly due to hormonal change. That is, once women reach menopause they experience a rapid decrease in estrogen level, and in particular, B-lymphocytes are produced in large quantity and thus pre-B cells are accumulated in bone marrow. As a result, the amount of IL-6 increases and thus the activity of osteoclasts increases thereby decreasing bone mass.

Accordingly, although there is a difference in its degree, aged people, especially post-menopausal women, cannot avoid osteoporosis, and in advanced countries with aging population, there is a growing interest in osteoporosis and therapeutic agents thereof.

Additionally, bone-related diseases also include osteoarthritis, bone loss diseases, etc., in addition to osteoporosis. Osteoarthritis is a disease in which a local degenerative change occurs as the cartilage of the joint becomes damaged, and also called degenerative arthritis. There are two main reasons for the occurrence of osteoarthritis, i.e., when joint tissue is damaged due to an overload on the joint although the cartilage or bone of the joint is normal, or when the cartilage or bone is weak although the load on the joint is normal.

Bone loss diseases may occur in many areas of the body, and major reasons of the bone loss diseases may include acute trauma accompanying bone tissue loss, acute trauma accompanying bone loss due to tissue removal during surgery, chronic infection accompanying bone resection, chronic nonunion accompanying segmental bone loss, etc.

There is established a global market associated with the treatment of bone diseases worth of at least about 130 billion US dollars and the size of the market is expected to continue to grow further in the future, and thus global research institutes and pharmaceutical companies have been investing much on the development of therapeutic agents for the treatment of bone diseases.

In particular, in the case of osteoporosis, for example, examples of osteoporosis treatments include androgenic anabolic steroids, calcium preparations, phosphates, fluorine preparations, ipriflavone, vitamin D3, etc. Merck & Co., Inc. (USA) developed aminobisphosphonate in 1953, Lilly Co. (USA) developed raloxifene, which serves as a selective estrogen receptor modulator (SERM), as therapeutic agents for treating osteoporosis.

Meanwhile, estrogen, which is a bone resorption inhibitor, is most widely used as a treatment for osteoporosis. However, a regular use of estrogen can increase the incidence rate of endometrial cancer and breast cancer, and can cause thrombosis, cholelithiasis, hypertension, edema, mastalgia, etc. The follow-up study on post-menopausal women, who were simultaneously administered with estrogen and progesterone, revealed a high incidence rate of breast cancer, stroke, pulmonary embolism, etc.

In addition, bisphosphonate preparations (alendronate and etidronate), vitamin D preparations, calcitonin preparations, calcium preparations, etc., are used as therapeutic agents for osteoporosis. However, these preparations have problems in that bisphosphonate preparations have a low absorption rate, a complicated administration method, causes esophagitis; vitamin D preparations are expensive and their effects have not been confirmed; calcitonin preparations are expensive and have a difficult method of administration; and calcium preparations have few adverse effects but they are effective for prevention rather than treatment of osteoporosis. Furthermore, osteoporosis cannot be treated by short-term administration of drugs but a long-term administration is essential. Accordingly, there is a need for the development of a novel material with excellent effect to replace the existing therapeutic materials without having the above adverse effects.

At present, for the bone morphogenetic activity, bone morphogenetic proteins (BMP), which belong to transforming growth factor (TGF)-β superfamily, have been reported (Science 150, 893-897, 1965; Science 242; 1528-1534, 1988). Known BMP species are from BMP-1 to BMP-14. Among them, BMP-2 to BMP-14 are known to exhibit bone morphogenetic activity. BMP-2 to BMP-14 are thought to be effective for the therapeutic treatment of various bone functional disorders and bone diseases but they are present in trace amounts in nature.

Accordingly, for obtaining BMP-2 to BMP-14, which are used for the above treatment, in large amount to make them affordable, the preparation of recombinant proteins are necessary. The preparation of recombinant proteins, in general, requires a higher expense compared to low molecular weight compounds. On the other hand, due to the proteinaceous characteristics, the recombinant proteins have many restrictions as pharmaceutical drugs from the aspects of physical properties and administration. Under these circumstances, the present inventors had previously developed Bone Peptide Protein 1 (BFP 1), which consists of 15 amino acids, as a low molecular weight organic compound having the same activity as that of BMP proteins.

SUMMARY

The present inventors have prepared and screened various kinds of human-derived proteins in order to prepare a peptide which has the same as or more excellent function or action than the native BMPs, can be produced at a low cost, and has excellent stability. As a result, a peptide which not only has excellent physiological activity but also has excellent stability was selected from many candidate peptides.

Accordingly, an aspect of the present invention is to provide a chemokine-derived peptide exhibiting the activity of differentiation factors via the promotion of differentiation by acting on osteoblasts or vascular endothelial cells.

Another aspect of the present invention is to provide a composition for ameliorating or treating the diseases or conditions of the effectiveness of osteogenic differentiation factor or bone morphogenetic factor or vascularization factor.

Still another aspect of the present invention is to provide a composition effective for ameliorating or treating vascular diseases including ischemic necrosis, which contains a peptide capable of exhibiting the activity of promoting vascularization as an active ingredient.

Still another aspect of the present invention is to provide a pharmaceutical composition, which has excellent pharmaceutical effects without adverse effects because it is a low molecular weight organic compound which contains a peptide consisting of 15 amino acids as an active ingredient, and also has a relatively low production cost.

Still another aspect of the present invention is to provide a culture composition for osteogenic differentiation which contains a peptide having the activity of osteogenic differentiation factor or bone morphogenetic factor, capable of controlling the bone morphogenesis speed according to the intention of an experimenter.

The purposes of the present invention are not limited to those described above, and other purposes and advantages of those not described above can be clearly understood by a skilled person in the art by the detailed description, claims, and drawings of the present invention described herein below.

In order to achieve the aspects described above, an embodiment of the present invention provides a peptide having the activity of a differentiation factor with an amino acid sequence of SEQ ID NO: 1.

In an embodiment, the peptide has a cell differentiation ability.

In an embodiment, the cell is an osteoblast or a vascular endothelial cell.

In an embodiment, the peptide is derived from SDF-1d protein.

Additionally, an embodiment of the present invention provides a pharmaceutical composition for treating or ameliorating osteoporosis containing any one of the peptides described above as an active ingredient.

Additionally, an embodiment of the present invention provides a pharmaceutical composition for treating or ameliorating osteoarthritis containing any one of the peptides described above as an active ingredient.

Additionally, an embodiment of the present invention provides a pharmaceutical composition for treating or ameliorating bone loss diseases containing any one of the peptides described above as an active ingredient.

Additionally, an embodiment of the present invention provides a culture medium for osteogenic differentiation containing any one of the peptides described above as an active ingredient.

Additionally, an embodiment of the present invention provides a pharmaceutical composition for treating or ameliorating vascular diseases containing any one of the peptides described above as an active ingredient.

In an embodiment, the vascular disease is ischemic necrosis.

The effects of one or more embodiments of the present invention are as follows.

First, the peptide of an embodiment of the present invention exhibits the activity of a differentiation factor by promoting differentiation by acting on osteoblasts or vascular endothelial cells.

Additionally, the peptide of an embodiment of the present invention can be used for ameliorating or treating the diseases or conditions of effectiveness of osteogenic differentiation factor or bone morphogenetic factor or vascularization factor.

Additionally, the peptide of an embodiment of the present invention is a low molecular weight organic compound consisting of 15 amino acids, which has excellent pharmaceutical effects without adverse effects and has a relatively low production cost.

Additionally, the pharmaceutical composition of an embodiment of the present invention can be effectively acted on for ameliorating or treating vascular diseases including ischemic necrosis by containing a peptide, which exhibits the activity of vascularization promoting factor, as an active ingredient.

Additionally, the pharmaceutical composition of an embodiment of the present invention can be effectively acted on for ameliorating or treating osteoporosis, osteoarthritis, or bone loss diseases by containing a peptide, which exhibits the activity of a differentiation factor, as an active ingredient.

Additionally, the composition for culture medium for osteogenic differentiation can control the osteogenic differentiation rate or bone morphogenetic rate according to the intention of the experimenter by containing a peptide, which exhibits the activity of a differentiation factor, as an active ingredient.

The effects of one or more embodiments of the present invention are not limited to those described above, and those effects which are not described will be clearly understood by a skilled person in the art based on the descriptions provided herein below.

DETAILED DESCRIPTION

The terms selected to be used in the present invention are those widely used at present in consideration of the functions, however, the terms may vary according to the intentions of a skilled person in the art or precedents, advent of new technologies, etc. Additionally, in particular cases, there are also terms randomly selected by the applicant, in which the terms will be explained in the detailed description of the present invention. Accordingly, the terms used in the present invention should be defined based on the meanings possessed by the terms and the contents of the present invention over the entire specification, instead of the simple names of the terms.

Hereinafter, the technical features of the present invention will be described in detail referring to the accompanying drawings and embodiments thereof. Unless otherwise specified, solid/solid refers to (weight/weight) parts or %, solid/liquid refers to (weight/volume) parts or %, and liquid/liquid refers to (volume/volume) parts or %.

However, the present invention may be restricted to embodiments explained herein below but may be embodied into different forms. Like numerals used for the explanation of the present invention over the entire specification represent like elements.

The present inventors have prepared and screened various kinds of human-derived proteins in order to prepare a peptide which has the same as or more excellent function or action than the native BMPs, can be produced at a low cost, and has excellent stability. As a result, a peptide which not only has excellent physiological activity but also has excellent stability was selected from many candidate peptides.

In particular, the present inventors have not synthesized the peptide of the present invention based on the region associated with the function of BMP but the technical feature of the present invention lies in that the peptide of the present invention was synthesized based on a particular region of human chemokines. That is, the peptide of the present invention was synthesized based on a partial region of the delta shape of stromal cell-derived factor 1 (SDF-1), known as C-X-C motif chemokine 12 (CXCL12).

In fact, chemokine is a cytokine selectively controlling cell adhesion of leukocyte subset, chemical attracting action, activation, etc., and is mainly involved in cell migration. Chemokine is a material having four conserved cysteine residues with a molecular weight of 10 kD (90 to 130 amino acids) and divided into two types (i.e., CC chemokine and CXC chemokine) according to the location of the two continuous cysteine residues, however, in fact, chemokine does not have the function of osteogenic differentiation.

Figure 1:
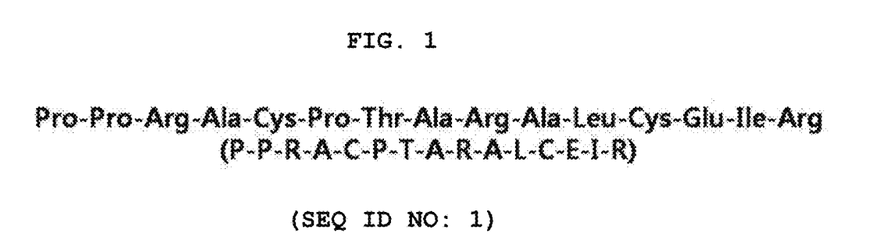
FIG. 1 shows the amino acid sequence of peptide BFP 5 of SEQ ID NO: 1.

The peptide of an embodiment of the present invention includes an amino acid sequence selected from the group consisting of SDF-1d-derived amino acids. In particular, the peptide of an embodiment of the present invention essentially consists of the amino acid sequence of SEQ ID NO: 1 illustrated in FIG. 1. The peptide of an embodiment of the present invention has a novel sequence consisting of 15 amino acids as illustrated in SEQ ID NO: 1, and the present inventors named the peptide of SEQ ID NO: 1 as bone forming peptide 5 (BFP 5).

As used herein, the term "peptide" refers to a linear molecule formed by amino acid residues interlinked by a peptide bond. The peptide of an embodiment of the present invention can be prepared according to a chemical synthesis method known in the art, and specifically, according to a solid-phase synthesis technique (Merrifield, J. Amer. Chem. Soc. 85:2149-54(1963); Stewart, et al., Solid Phase Peptide Synthesis, 2nd. ed., Pierce Chem. Co.: Rockford, 111 (1984)).

The peptide of SEQ ID NO: 1 performs an action similar to at least one of native BMP and chemokine, and performs a function such as a differentiation factor by binding to a receptor. In particular, the peptide of SEQ ID NO: 1 plays a role of promoting the differentiation of osteoblasts or vascular endothelial cells.

The peptide of an embodiment of the present invention not only exhibits an excellent physiological activity almost the same as or more excellent than that of native BMP or chemokine, but also has excellent thermal stability and stability to physicochemical factors such as acids, alkalis, etc. Accordingly, the peptide of an embodiment of the present invention having the excellent long-term preservation can be advantageously applied to products which require long-term storage, such as pharmaceutical drugs and quasi-drugs.

The peptide of an embodiment of the present invention may be contained in a pharmaceutical composition as an active ingredient.

Accordingly, the pharmaceutical composition of an embodiment of the present invention is a pharmaceutical composition including (a) a pharmaceutically effective amount of the peptide of the present invention; and (b) a pharmaceutically acceptable carrier.

As used herein, the term "pharmaceutically effective amount" refers to an amount sufficient to achieve the effect or activity of the peptide described above.

The pharmaceutically acceptable carrier to be contained in the pharmaceutical composition of the present invention is that which is conventionally used in preparation, and may include lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methyl cellulose, methylhydroxybenzoate, propylhydroxybenzoate, talc, magnesium stearate, mineral oil, etc., but is not limited thereto. The pharmaceutical composition of an embodiment of the present invention may further include a lubricant, a humectant, a sweetener, a fragrant, an emulsifier, a suspending agent, a preservative, etc., in addition to the above components. Examples of the appropriate pharmaceutically acceptable carriers and formulations are described in detail in Remington's Pharmaceutical Sciences (19th ed., 1995).

The pharmaceutical composition of an embodiment of the present invention may be administered orally or parenterally, and preferably, parenterally. For parenteral administration, the pharmaceutical composition may be administered via intravenous injection, subcutaneous injection, intramuscular injection, intraperitoneal injection, local administration, transdermal administration, etc.

The appropriate dose of the pharmaceutical composition of an embodiment of the present invention may be prescribed variously according to factors such as formulation method, administration method, age, body weight, and sex of a patient, severity of disease, diet, administration time, administration route, excretion rate, and sensitivity to responses. Meanwhile, the dose of the pharmaceutical composition of an embodiment of the present invention is 0.0001 μg/day to 100 μg/day, and, for example, 0.0001 μg/mL to 1 μg/mL.

The pharmaceutical composition of an embodiment of the present invention may be prepared in a unit dose form or encapsulated into a multi-dose container, according to the method that a skilled person in the art can easily perform, by formulating the pharmaceutically acceptable carrier and/or excipient. In particular, the formulation may be in the form of a solution in oil or an aqueous medium, a suspension or emulsion, or an extract, powder, granules, a tablet, or a capsule, and may further include a dispersant or a stabilizer.

EXAMPLE

Synthesis of Pro-Pro-Arg-Ala-Cys-Pro-Thr-Ala-Arg-Ala-Leu-Cys-Glu-Ile-Arg (SEQ ID NO: 1)

Chloro trityl chloride resin (CTL resin, Nova Biochem Cat. No. 01-64-0021) in an amount of 700 mg and 10 mL of methylene chloride (MC) were added to a reaction container and stirred for 3 minutes. After removing the solution, 10 mL of dimethylformamide (DMF) was added thereto and stirred for 3 minutes, and the solvent was removed. Dichloromethane (10 mL), 200 mmole of Fmoc-Arg(pbf)-OH (Bachem, Switzerland) and 400 mmole of diisopropylethylamine (DIEA) were added to the reaction container and well dissolved by stirring, and reacted while stirring for an hour. Upon completion of the reaction, the resultant was washed, and reacted with methanol and DIEA (a 2:1 ratio) dissolved in dichloromethane (DCM) for 10 minutes and washed with an excess amount of DCM/DMF (a 1:1 ratio). After removing the solution, 10 mL of dimethylformamide (DMF) was added thereto and stirred for 3 minutes, and the solvent was removed. A deprotection solution (20% of piperidine/DMF) in an amount of 10 mL was added to the reaction container, stirred at room temperature for 10 minutes, and the solution was removed. An equal amount of the deprotection solution was added thereto and the reaction was maintained for 10 minutes, and the solution was removed and washed twice with DMF, once with MC, and once with DMF for 3 minutes, respectively, and the Arg(pbf)-CTL Resin was prepared therefrom.

DMF solution (10 mL), 200 mmole of Fmoc-Ile-OH (Bachem, Switzerland), 200 mmole of HoBt, and 200 mmole of Bop were added to a new reaction container, and well dissolved by stirring. DIEA (400 mmole) was added twice in fractions to the reaction container and stirred for at least 5 minutes until all the solids became dissolved. The dissolved amino acid mixture solution was added into the reaction container, in which the deprotected resin is included, and reacted at room temperature for an hour while stirring. The reaction solution was removed and stirred 3 times with DMF solution for 5 minutes each time and removed. A small amount of the reacted resin was collected and the degree of the reaction was examined by Kaiser test (Nihydrin test). The deprotection reaction was performed twice using the deprotection solution in the same manner as described above and Ile-Arg(pbf)-CTL resin was prepared therefrom. The resin was sufficiently washed with DMF and MC, and subjected again to the Kaiser test, and the following amino acid adhesion test was performed in the same manner as described above. Based on the selected amino acid sequences, chain reactions were performed in the order of Fmoc-Glu, Fmoc-Cys(trt), Fmoc-Leu, Fmoc-Ala, Fmoc-Arg, Fmoc-Ala, Fmoc-Thr, Fmoc-Pro, Fmoc-Cys(trt), Fmoc-Ala, Fmoc-Arg, Fmoc-Pro, and Fmoc-Pro. The Fmoc-protecting group was reacted twice with a deprotection solution for 10 minutes each time and removed by washing well. Acetic anhydride, DIEA, and HoBt were added thereto to perform acetylation for an hour, and the peptidyl resin was washed 3 times with DMF, MC, and methanol, respectively, dried by slowly flowing nitrogen air thereto, completely dried by reducing to vacuum under P2O5, and added with 30 mL of dehydration solution (tifluroacetic acid (95%), distilled water (2.5%), an thioanisole (2.5%)) and the reaction was maintained at room temperature for 2 hours while occasionally shaking. The resin was filtered via filtration, washed with a small amount of TFA solution, and combined with the mother liquor. The resultant was distilled until the entire volume was reduced to about a half under reduced pressure, and precipitation was induced by adding 50 mL of cold ether. The precipitates were collected by centrifugation and washed twice with colder ether. After removing the mother liquor, the resultant was sufficiently dried under nitrogen and 0.65 g of NH2-Pro-Pro-Arg-Ala-Cys-Pro-Thr-Ala-Arg-Ala-Leu-Cys-Glu-Ile-Arg-OH peptide was synthesized before purification (yield: 93%).

Experimental Example 1

The structure of SEQ ID NO: 1 prepared in Example was confirmed by adding 15 amino acid sequences using the program provided by on-line PEP-FOLD server. The results are shown in FIG. 2.

Figure 2:
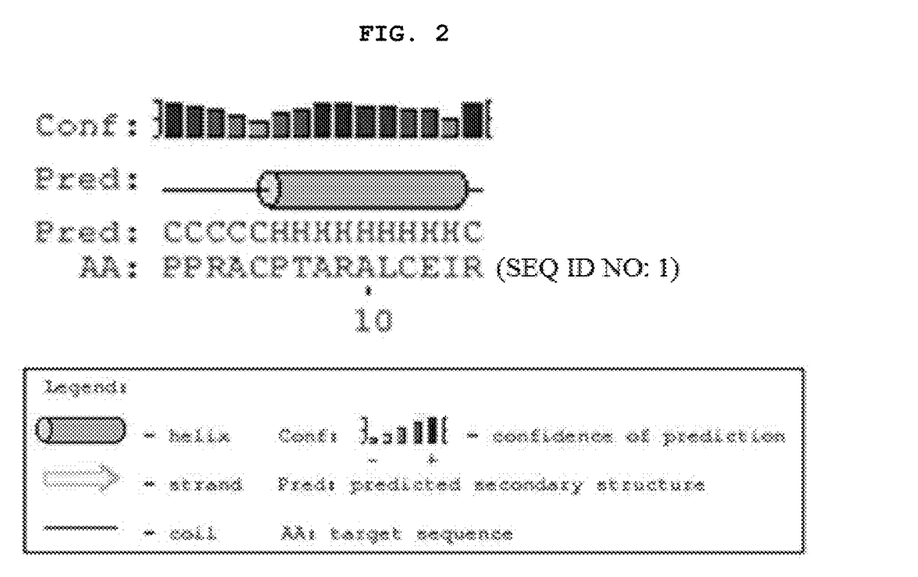
FIG. 2 shows the structure of peptide BFP 5 of SEQ ID NO: 1 of an embodiment of the present invention.

From FIG. 2, it was observed that the peptide with SEQ ID NO: 1 has an α-helix structure.

Experimental Example 2

For the confirmation of the effect of BFP 5, which is a peptide of SEQ ID NO: 1 prepared in Example, on the activity of osteogenic differentiation, the following experiment was performed.

1. Preparation of Osteoblasts and a Medium for Osteogenic Differentiation

Mesenchymal stem cells ($1 \times 10^4$), which were cloned from Balb/c mouse bone marrow stromal cells) were aliquoted into 10% FBS-containing DMEM and cultured in an atmosphere (about 37° C., 5% $CO_2$) for 3 days, and thereby the mesenchymal stem cells to be used as osteoblasts in the present experiment were prepared. Osteogenic differentiation medium (hereinafter, "ODM") consists of DMEM which contains 50 μg/mL of ascorbic acid, $10^{-8}$ M dexamethasone, 10 mM β-glycerophosphate, etc.

2. Measurement of Mineralization

The differentiation of the mesenchymal stem cells into osteoblasts causes calcium accumulation. Here, the degree of calcium accumulation refers to the degree of differentiation of osteoblasts, and the degree of accumulation of calcium ions can be confirmed by observing the degree of staining of the cells that are stained red, via Alizarin Red staining. In this regard, the mineralization was measured via Alizarin Red staining. That is, as the differentiation into osteoblasts are promoted there are more regions that can be stained by Alizarin Red. Accordingly, the degree of osteogenic differentiation can be confirmed by adding Alizarin Red to the osteogenic differentiation medium, treating with the peptide of SEQ ID NO: 1 (BFP 5), and observing the degree of Alizarin Red staining.

More specifically, the prepared osteoblasts, i.e., mesenchymal stem cells, were transferred to the osteogenic differentiation medium, and added with BFP 5 at concentrations of 0.01 µg/µL, 0.1 µg/µL, 1 µg/µL, and 10 µg/µL, and incubated for two additional days. Then, the cultured mesenchymal stem cells were cooled on ice, fixed with 70% ethanol for an hour, and stained with Alizarin Reds solution for about 10 minutes, and the mineralization was confirmed by the degree of calcium deposition. The results are shown in FIG. 3.

Figure 3:
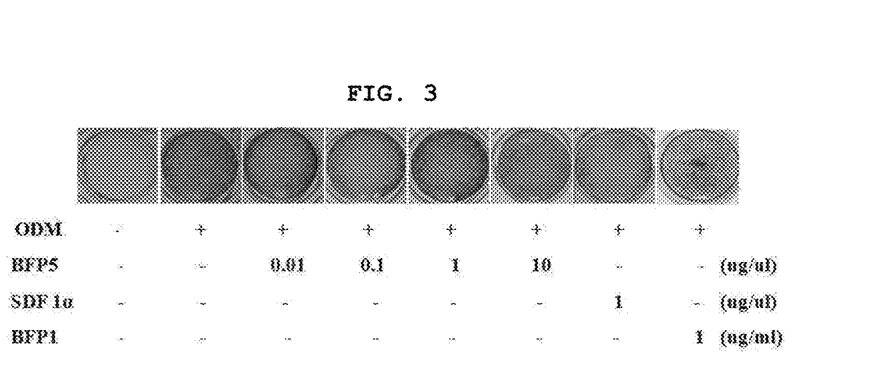
FIG. 3 shows a picture of mineralization accumulated via osteogenic differentiation by BFP 5 confirmed by Alizarin Red staining.

As confirmed by Alizarin Red staining which measures the mineralization being accumulated via osteogenic differentiation by BFP 5, which is the peptide of SEQ ID NO: 1 of an embodiment of the present invention, from the picture in FIG. 3, it was confirmed that the cells added with 1 µg/µL, of BFP 5 showed the strongest staining. Additionally, when the osteogenic differentiation was confirmed using BFP 1, the staining was equal to or weaker compared to the BFP 5. Additionally, although the osteogenic differentiation ability of chemokine SDF 1a has not been known, a weak staining was confirmed as a result of the experiment, and thus it is speculated that chemokine SDF 1α can promote the osteogenic differentiation. Accordingly, it can be concluded that BFP 5, which is a synthetic peptide derived from chemokine has the ability of promoting osteogenic differentiation being equal to or higher than that of BFP 1, which is a synthetic peptide derived from BMP-7.

Experimental Example 3

Figure 4:
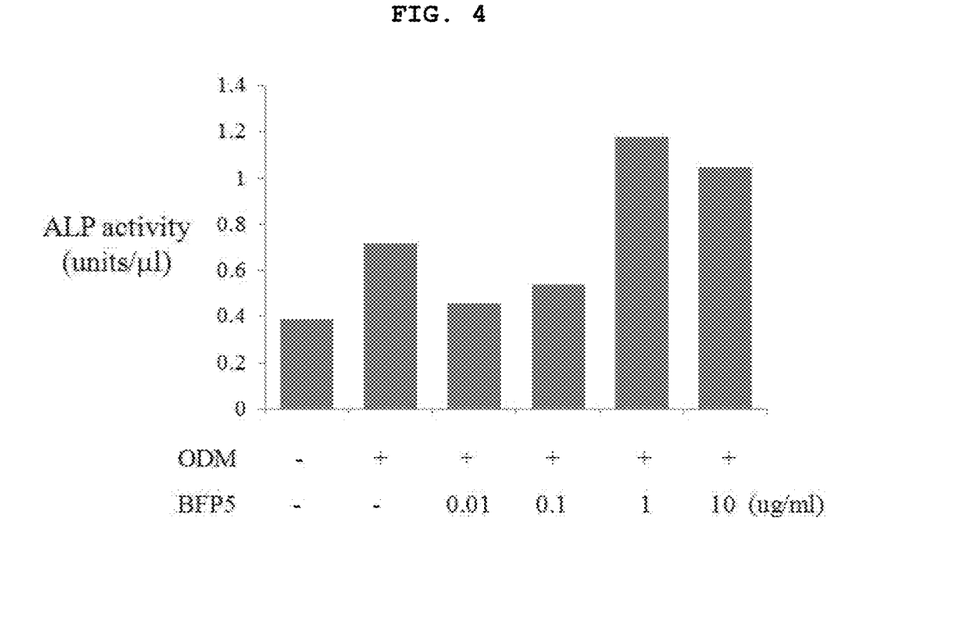
FIG. 4 shows a graph illustrating the experimental result of measuring the expression level of alkaline phosphatase, an osteoblast-specific gene, by BFP 5.

An experiment to measure the expression level of alkaline phosphatase, which is an osteoblast-specific gene by BFP 5, which is a peptide of SEQ ID NO: 1 prepared in Example, was performed to measure the enzyme activity of alkaline phosphatase using a kit, and the result is shown in FIG. 4. An osteoblast-specific gene is expressed upon differentiation into osteoblasts, and in particular, the expression level of alkaline phosphatase, which is an osteoblast-specific gene, was measured by reverse transcription gene amplification (RT-PCR), and as a result, it was confirmed that a strong expression of alkaline phosphatase was observed at 1 µg/µL of BFP 5.

Experimental Example 4

Figure 5:
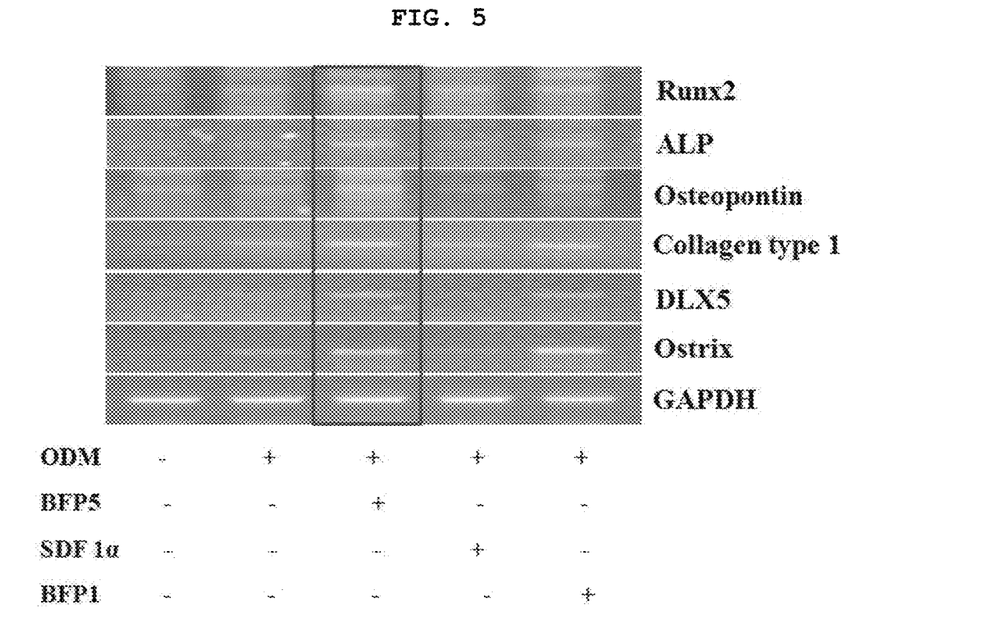
FIG. 5 shows a picture illustrating the experimental result of measuring the expression level of Runx2, alkaline phosphatase, Osteopontin, collagen type 1, DLX5, and Osterix, which are osteoblast-specific genes, by BFP 5.

In order to confirm the effect of BFP 5, which is a peptide of SEQ ID NO: 1 prepared in Example, on the activity of osteogenic differentiation, the expression levels of osteoblast-specific genes, e.g., Runx2, alkaline phosphatase, Osteopontin, collagen type 1, DLX5, and Osterix, by BFP 5 were analyzed under a fluorescent microscope using antibodies, and the resulting pictures are shown in FIG. 5, respectively.

From FIG. 5, it was confirmed that the genes of Runx2, alkaline phosphatase, Osteopontin, collagen type 1, DLX5, and Osterix, which are expressed in osteoblasts, are strongly expressed in the cells treated with BFP 5.

An osteoblast-specific protein is expressed upon differentiation into osteoblasts. When the antibody to the protein was reacted to cells and the degree of binding was confirmed by a fluorescent microscope. As a result, it was confirmed that alkaline phosphatase, which is an enzyme used as a marker for osteogenesis and is produced during the mid-stage of osteogenic differentiation, was strongly expressed in BFP 5, and also Runx-2, which is a transcription regulatory factor playing an important role in the production of osteoblast-specific proteins in osteoblasts, performs an important role in osteogenic differentiation. The Runx-2 was also shown to be strongly expressed in BFP 5.

Experimental Example 5

Figure 6:
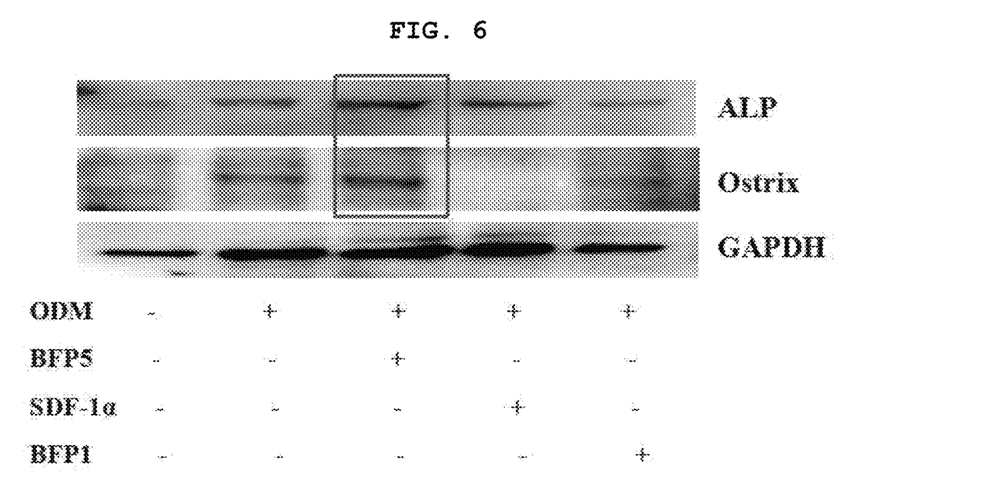
FIG. 6 shows a picture illustrating the experimental result of measuring the expression level of alkaline phosphatase and Osterix, which are proteins expressed in osteoblast, by BFP 5.

In order to confirm the effect of BFP 5, which is a peptide of SEQ ID NO: 1 prepared in Example, on the activity of osteogenic differentiation, the level of proteins expressed in osteoblasts were confirmed and the results are shown in FIG. 6.

As illustrated in FIG. 6, it was observed that alkaline phosphatase and Osterix were strongly expressed by BFP 5.

Experimental Example 6

Figure 7:
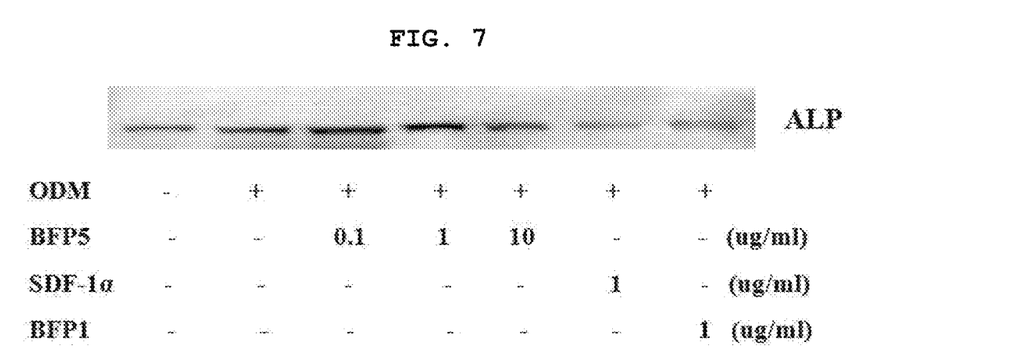
FIG. 7 shows a picture illustrating the expression level of alkaline phosphatase, which is a protein expressed in osteoblast, after treating with varied concentrations of BFP 5.

In order to confirm the effective concentration of BFP 5, which is a peptide of SEQ ID NO: 1 prepared in Example, on the activity of osteogenic differentiation, cells were treated with BFP 5 at varied concentrations and the expression level of alkaline phosphatase, which is expressed in osteoblasts, and the results are shown in FIG. 7.

From FIG. 7, it was confirmed that when BFP 5, which affects the activity of osteogenic differentiation, is treated at a concentration from 0.1 µg/mL to 1.1 µg/mL the osteoblasts are expressed at the highest level.

Experimental Example 7

Figure 8:
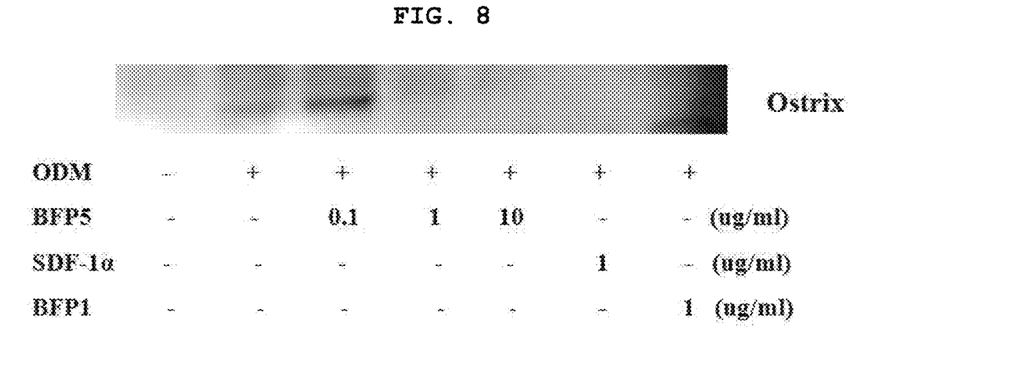
FIG. 8 shows a picture illustrating the expression level of Osterix, which is a protein expressed in osteoblast, after treating with varied concentrations of BFP 5.

In order to confirm the effective concentration of BFP 5, which is a peptide of SEQ ID NO: 1 prepared in Example, on the activity of osteogenic differentiation, cells were treated with BFP 5 at varied concentrations and the expression level of Osterix, which is expressed in osteoblasts, and the results are shown in FIG. 8.

From FIG. 8, it was confirmed that when BFP 5, which affects the activity of osteogenic differentiation, was treated at a concentration of 0.1 µg/mL, the osteoblasts were expressed at the highest level.

Experimental Example 8

In order to confirm the effect of BFP 5, which is a peptide of SEQ ID NO: 1 prepared in Example, on the activity of vascularization, cells were treated with BFP 5 along with VEGF, FGF, SDF-1a, and SDF-1g, and the effect of BFP 5 on vascularization was observed. The results are shown in FIG. 9.

Figure 9:
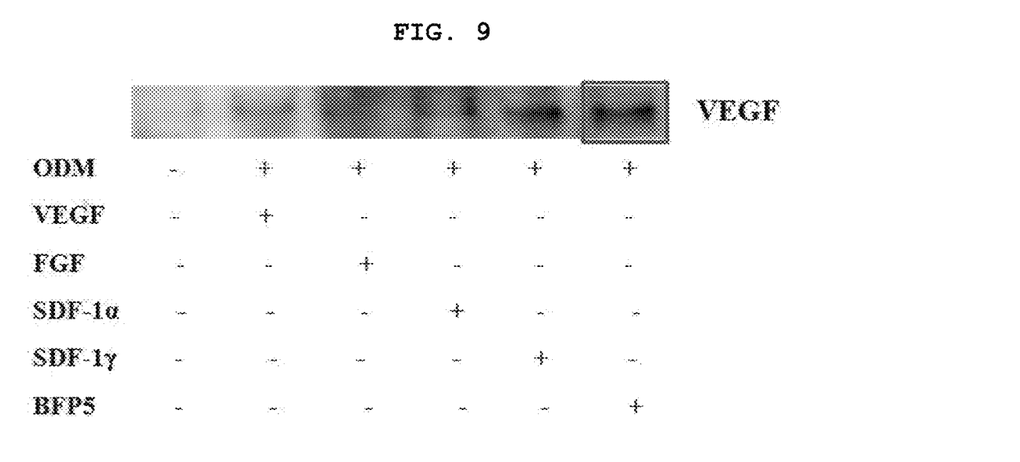
FIG. 9 shows a picture illustrating the effect of BFP 5 on vascularization by treating cells with BFP 5 along with VEGF, FGF, SDF-1a, and SDF-1g.

From FIG. 9, in which the expression of VEGF, a protein associated with vascularization, was confirmed, it was confirmed that cells treated with BFP 5 showed a strong expression of VEGF.

From the results of these experiments, it can be confirmed that since BFP 5, which is a peptide of SEQ ID NO: 1 of an embodiment of the present invention, has a more important effect on the promotion of osteogenic differentiation than BMP-7 or BFP 1, which were previously known to promote osteogenic differentiation, it is certain that BFP 5 can induce rapid osteogenesis in a wider range having the osteogenesis intensity the same as or higher than that of BMP-7. Additionally, it is obvious that BFP 5, which is a peptide of SEQ ID NO: 1 of an embodiment of the present invention, has the osteogenesis-promoting functionality the same as or higher than that of BFP 1 in a treatment concentration significantly lower than that of BFP 1.

As a result, the pharmaceutical composition of an embodiment of the present invention can be acted as an effective therapeutic agent for osteoporosis and/or osteoarthritis. Additionally, in the same manner, when the pharmaceutical composition of an embodiment of the present invention is filled or administered into the bone loss areas of bone loss diseases, bone recovery can be effectively performed by promoting osteogenesis. Additionally, the pharmaceutical composition of an embodiment of the present invention can be acted as an effective therapeutic agent for ameliorating or treating vascular diseases including ischemic necrosis by containing a peptide exhibiting the activity of promoting vascularization as an active ingredient.

Meanwhile, although specific embodiments are not provided, it is obvious that when BFP 5, which is a peptide of SEQ ID NO: 1 of an embodiment of the present invention, is added to a culture composition for osteogenic differentiation, the experimenter can control the speed of the experiment while performing the experiment thus capable of easily performing the experiment.

The present invention has been explained referring to the exemplary embodiments. However, the scope of the present invention shall not be restricted to these embodiments, and various modifications and improved forms by one of ordinary skill in the art using the basic concept of the present invention defined in the appended claims are to be embraced within the scope of the present invention.

What is claimed is:

1. A culture medium composition for a differentiation of osteoblast, comprising:
    a peptide exhibiting the activity of a differentiation factor, wherein the peptide is a synthetic peptide and the peptide consists of the amino acid sequence of PPRACPTARALCEIR (SEQ ID NO: 1) as an active ingredient;
    ascorbic acid;
    dexamethasone; and
    β-glycerophosphate.

2. The composition of claim 1, further comprising a pharmaceutical acceptable carrier selected from the group consisting of lactose, dextrose, sucrose, sorbitol, mannitol, starch, microcrystalline cellulose, polyvinyl pyrrolidone, cellulose, syrup, and methyl cellulose.

3. The composition of claim 1, further comprising a pharmaceutical acceptable carrier selected from the group consisting of acacia rubber, calcium phosphate, alginate, gelatin, calcium silicate, methylhydroxybenzoate, propylhydroxybenzoate, talc, magnesium stearate, and mineral oil.

4. The composition of claim 1, further comprising:
    at least one selected from the group consisting of a lubricant, a humectant, a sweetener, a fragrant, an emulsifier, a suspending agent, and a preservative.

5. A pharmaceutical composition comprising the composition of claim 1.

6. The pharmaceutical composition of claim 5, wherein a form of the pharmaceutical composition is one selected from the group consisting of a solution in oil, a suspension, an emulsion, an extract, powders, granules, a tablet, and a capsule.

* * * * *